US00PP08239P

United States Patent [19]

Ronald

[11] Patent Number: Plant 8,239

[45] Date of Patent: May 25, 1993

[54] LITTLE LEAF LINDEN—RONALD CULTIVAR

[75] Inventor: Wilbert G. Ronald, Portage la Prairie, Canada

[73] Assignee: Bailey Nurseries, Inc., St. Paul, Minn.

[21] Appl. No.: 690,862

[22] Filed: Apr. 24, 1991

[51] Int. Cl.[5] ..... A01H 5/00
[52] U.S. Cl. ..... Plt./53.4
[58] Field of Search ..... Plt./51, 53.4

[56] References Cited

U.S. PATENT DOCUMENTS

P.P. 3,259 8/1972 McIntyre ..... Plt. 51

OTHER PUBLICATIONS

Weiner, M. "Plant Hardiness Zone Map"; Linden, little leaf *Plant a Tree,* Collier Books, N.Y. 1975 pp. 109, 204, 205.

*Primary Examiner*—James R. Feyrer
*Attorney, Agent, or Firm*—Burns, Doane, Swecker & Mathis

[57] ABSTRACT

A new and distinctive cultivar of little leaf linden, botanically known as *Tilia cordata* is provided. The new cultivar exhibits a more rapid growth rate than is commonly observed in the species, exhibits superior winter hardiness in northern zones, and exhibits good foliage disease resistance. The crown is moderately pyramidal in configuration, and the trunk is sturdy and well resists sun scald. Flowers are formed in abundance, but lead to the formation of a sparse seed crop. The new cultivar is particularly suited for use as an attractive landscape planting and for use in areas where a distinctive shade tree is desired.

2 Drawing Sheets

SUMMARY OF THE INVENTION

The original tree of the new cultivar of *Tilia cordata* was selected during 1983 from a group of open-pollinated seedlings being evaluated by me at Portage la Prairie, Manitoba, Canada. The seedlings were produced from seed obtained from an unnamed extremely hardy *Tilia cordata* tree being grown since 1942 at the Morden Research Station, Morden, Manitoba, Canada. The origin of the female parent tree (i.e., the seed parent tree) can be traced to Manchuria, China, where it was obtained by Dr. Frank Skinner during the late 1930's. The identity of the male parent tree (i.e., the pollen parent tree) is unknown. However, it appears likely that the pollen employed in the creation of the new cultivar was derived from any one of a number of more typical *Tilia cordata* trees from less hardy European sources. I was attracted to a single tree of the new cultivar which exhibited a number of outstanding characteristics as discussed hereafter. Had I not discovered, evaluated, and preserved the new cultivar, it would have been lost to mankind.

Budwood obtained from the original tree of the new cultivar has been budded onto regular *Tilia cordata* little leaf linden seedling understock at Jeffries Nurseries Ltd., Manitoba, Canada, and at Bailey Nurseries Inc., Yamhill, Oreg., U.S.A. These and subsequent propagations have well confirmed the distinctiveness of the new cultivar when grown under different environmental settings.

It was found that the following combination of characteristics is exhibited by the new cultivar of *Tilia cordata:*

(a) exhibits a relatively rapid growth rate to form an attractive symmetrical tree having a moderately pyramidal crown and study lateral branches, (b) exhibits improved winter hardiness in northern zones and a high degree of trunk tolerance to winter sun scald damage,
(c) forms attractive dark green foliage which exhibits good resistance to leaf gall mites and fungal leaf spotting, and
(d) forms fragrant flowers in abundance which tend to form a sparse seed crop.

The new cultivar has been continuously evaluated for its horticultural performance from the time of its initial selection. The characteristics of the new variety have been found to be stably manifest and to provide a distinctive new cultivar which is well suited to provide an attractive planting in the landscape. An attractive new shade tree is provided.

The new little leaf linden cultivar has been named the Ronald cultivar, and will be marketed by Bailey Nurseries Inc. of St. Paul, Minn., U.S.A., and its licensees, and by Jeffries Nurseries Ltd. of Portage la Prairie, Manitoba, Canada, under the Norlin trademark.

BRIEF DESCRIPTION OF THE PHOTOGRAPHS

The accompanying photographs show the original tree of the new cultivar of *Tilia cordata* as depicted in color as true as is reasonably possible to make the same in color illustrations of this character. The tree was growing at Portage la Prairie, Manitoba, Canada.

DETAILED DESCRIPTION OF THE NEW CULTIVAR

Figure 1:
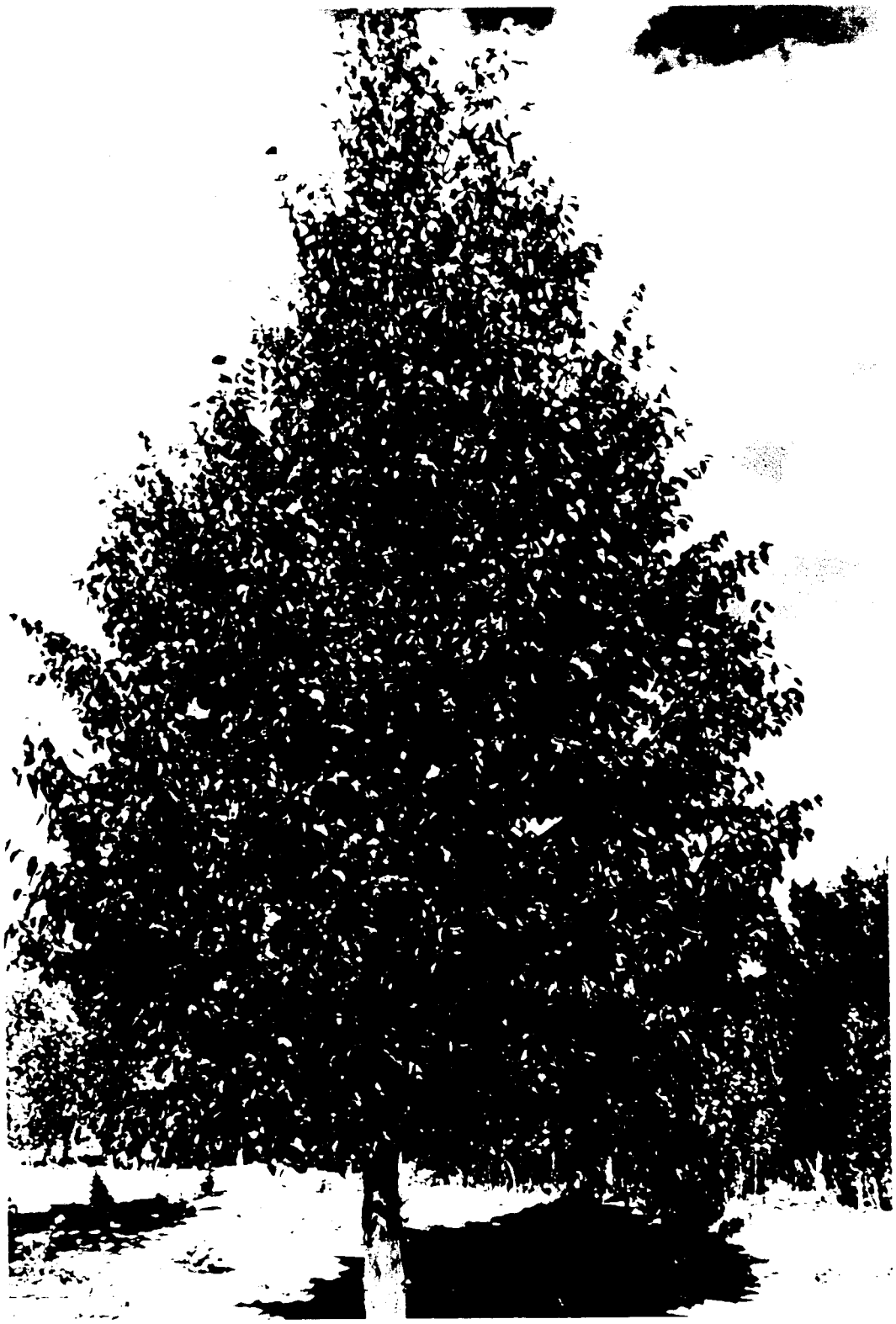
FIG. 1 illustrates the attractive dark green foliage and the moderately pyramidal crown of the new cultivar during July, 1990.

The following description of the new cultivar of *Tilia cordata* is based upon the observation of the original tree being grown at Portage la Prairie, Manitoba, Canada, as well as upon the study of its asexually budded progeny. The color terms are with reference to the R.H.S. Colour Chart of The Royal Horticultural Society, London, England, and general color terms are to be accorded their ordinary dictionary significance.

The new cultivar has been found to exhibit a superior growth rate when compared to that commonly associated with *Tilia cordata.* For instance, when the rate of growth for the new cultivar is compared to that of a standard linden cultivar growth in northern areas (e.g., hybrid *Tilia flavescens,* Dropmore linden), it is found to exhibit a growth rate which is approximately 30 to 40 percent faster. The Dropmore linden is recognized to be a fast-growing hybrid linden tree which commonly is grown at the same area where the new cultivar of the present invention originated. This more rapid growth rate will enable the formation of a tree of larger grade under similar tree production systems and will thereby benefit the nurseryman as well as the ultimate consumer.

Growth measurements were obtained for the new cultivar, common little leaf linden seedlings, and the Dropmore cultivar for comparative purposes while grown under nursery conditions at Portage la Prairie, Manitoba, Canada. The growth measurements are reported below:

| | Growth First Year | Total Growth After Second Year |
|---|---|---|
| RONALD cultivar | 67.4 in. | 95.9 in. |
| Common little linden seedling | 38.2 in. | 57.1 in. |
| Dropmore linden | 48.6 in. | 70.1 in. |

The values obtained for the first year were obtained from an average of 10 trees, and the values obtained after the second year were obtained from an average of 20 trees.

Also, the more rapid growth rate of the Ronald cultivar has been confirmed during the first year of growth from the bud in replicated field plantings of the North Dakota State University Horticulture and Forestry Cooperative Testing Program at Bismarck, Fargo and Grand Forks, N. D., U.S.A. Such test plantings included the Corinthian and Shamrock linden cultivars. The mean growth values for all three locations are presented below:

| | Growth First Year |
|---|---|
| RONALD cultivar | 6.2 in. |
| CORINTHIAN cultivar | 3.5 in. |
| SHAMROCK cultivar | 1.9 in. |

The original tree of the new cultivar has assumed a trunk diameter at one foot above the ground of approximately 8 in., and a height of approximately 20 feet. Since this tree was transplanted while at an age of approximately 9 years to a nearby location, its subsequent growth has been retarded as it becomes reestablished. Accordingly, these dimensions are somewhat less than what would be anticipated had the tree not been transplanted. Two year-old trees of the new cultivar commonly assume a trunk diameter at one foot above the ground of approximately 1 to 1¼ in. and a height of approximately 8 feet.

Figure 2:
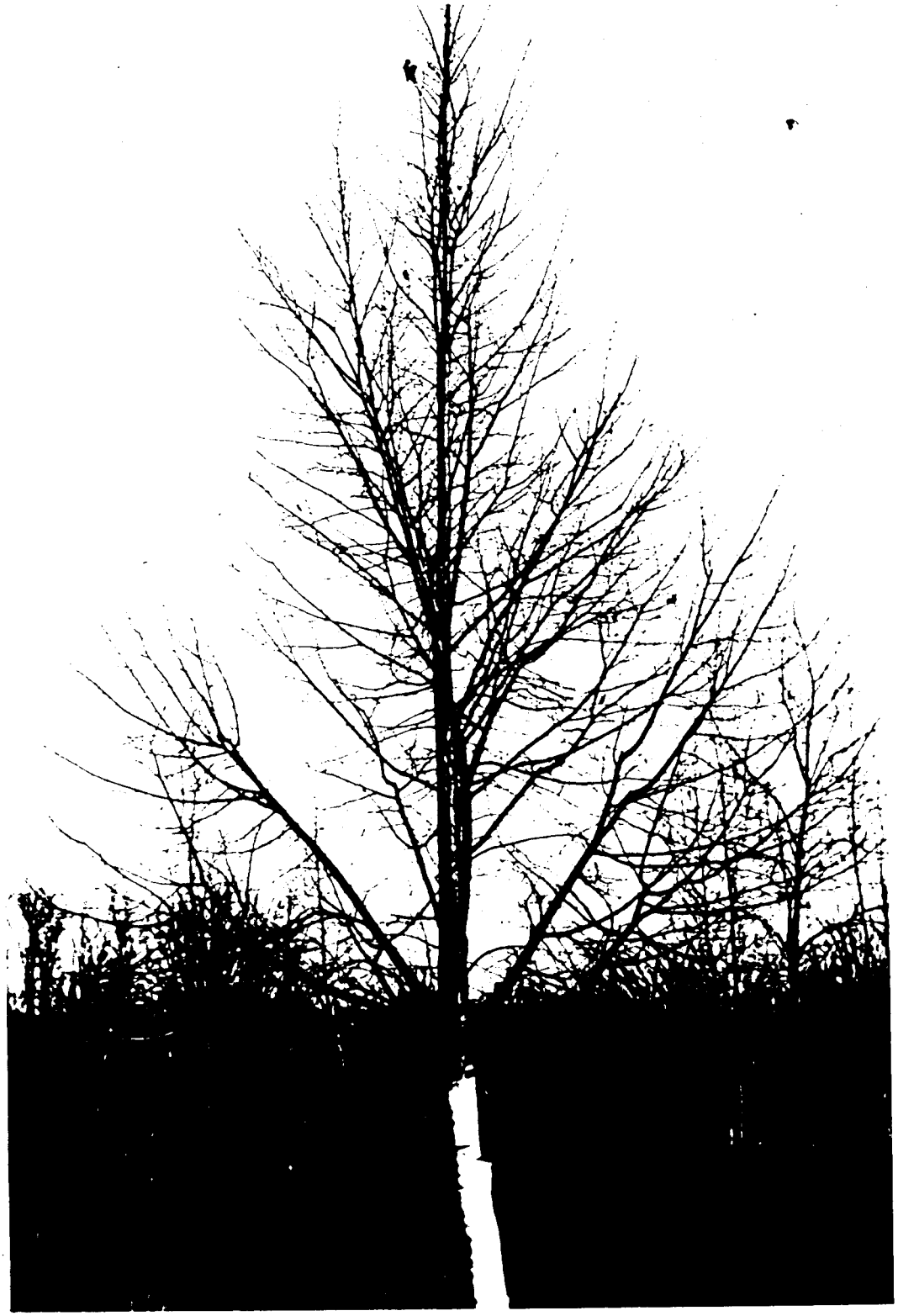
FIG. 2 illustrates the dormant tree during November, 1990, wherein the dominant central leader and sturdy lateral branches are clearly visible.

As illustrated in FIGS. 1 and 2, the new cultivar tends to form a dominant strong central leader upon which are borne studry lateral branches. The lateral branches commonly leave the central leader at an angle of approximately 45 degrees (as illustrated) thereby producing relatively strong crotches. The overall configuration of the tree crown is moderately pyramidal (as illustrated). The sturdiness of the branches of the new cultivar has been found to at least equal or to exceed that the Dropmore cultivar as well as the other cultivars of *Tilia cordata.* No winter limb breakage because of snow accumulation has been observed to date.

Superior winter hardiness has been observed in the new cultivar even when grown in northern regions such as Portage la Prairie, Manitoba, Canada. Accordingly, the trunk section of the tree has been found to escape the usual sun scald damage to which *Tilia cordata* commonly is susceptible under such growing conditions. The new cultivar has successfully withstood a temperature of −35.5° F. without any damage. Such extreme temperatures commonly cause trunk damage and branch tip damage to other little leaf linden trees.

The new cultivar forms attractive dark green leaves which tend to be larger than those typically formed by *Tilia cordata.* More specifically, the leaves are about 25 percent larger than those of the typical *Tilia cordata* and commonly measure 3 to 3½ inches in length. Otherwise the appearance of the leaves is generally comparable to those of the typical *Tilia cordata* trees with substantially the same leaf cuticle thickness being observed. The foliage of the new cultivar has retained a healthy appearance and shows freedom from damage by leaf gall mites and fungal spots. Damage by leaf gall mites and fungal spots commonly is a major problem with typical *Tilia cordata* trees. The foliage tends to mature ahead of that of the regular *Tilia cordata* and is maintained late in fall. During most autumns the foliage of the new cultivar assumes an attractive golden coloration.

One year-old dormant winter twigs of the new cultivar commonly assume the coloration of Greyed-Orange Group 175A to 175C, and two year-old dormant winter twigs commonly assume the coloration of Grey-Brown Group 199A. Also, the buds when observed during the winter commonly assume the coloration of Greyed-Orange Group 175A.

On more established trees of the new cultivar the bark tends to be somewhat rougher than that typically observed on *Tilia cordata* trees. Also, the bark on such trees commonly is of a slightly darker gray-brown coloration than that observed on typical *Tilia cordata* trees.

The flowers of the new cultivar are fragrant and are borne in abundance. Such flower abundance makes a significant contribution to ornamental appearance of the new cultivar in the landscape. However, seed production on the new cultivar has been sparse thereby contributing to a clean fall appearance and reducing the fall stress commonly associated with the species which is influenced by the demands placed upon the tree in the support of heavy seed production. The sparse seed production is believed to be attributable to undefined physiological factors which are complex and incapable of definition. Such factors may be attributable to the likely genetic dissimilarity of the parents of the new cultivar.

I claim:

1. A new and distinct cultivar of *Tilia cordata* tree, having the following combination of characteristics:

(a) exhibits a relatively rapid growth rate to form an attractive symmetrical tree having a moderately pyramidal crown and sturdy lateral branches, (b) exhibits improved winter hardiness in northern zones and a high degree of trunk tolerance to winter sun scald damage, (c) forms attractive dark green foliage which exhibits good resistance to leaf gall mites and fungal leaf spotting, and (d) forms fragrant flowers in abundance which tend to form a sparse seed crop;

substantially as illustrated and described.

* * * * *